United States Patent
Richter et al.

(10) Patent No.: US 9,862,723 B2
(45) Date of Patent: Jan. 9, 2018

(54) STABLE POLYMORPH OF THE SALT OF (2R)-4-OXO-4-[3-(TRIFLUOROMETHYL)-5,6-DIHYDRO[1,2,4]TRIAZOLO[4,3-α]PYRAZIN-7(8H)-YL]-1-(2,4,5-TRIFLUOROPHENYL)BUTAN-2-ANIME WITH L-TARTARIC ACID

(71) Applicant: ZENTIVA k.s, Prague (CZ)

(72) Inventors: Jindrich Richter, Pardubice (CZ); Petr Lehnert, Prague (CZ); Kamal Jarrah, Prague (CZ); Ondrej Dammer, Hostivice (CZ); Lukas Krejcik, Praha-Vinor (CZ)

(73) Assignee: Zentiva k.s., Praha (CZ)

( * ) Notice: Subject to any disclaimer, the term of this patent is extended or adjusted under 35 U.S.C. 154(b) by 0 days.

(21) Appl. No.: 15/030,879

(22) PCT Filed: Oct. 30, 2014

(86) PCT No.: PCT/CZ2014/000125
§ 371 (c)(1),
(2) Date: Apr. 21, 2016

(87) PCT Pub. No.: WO2015/062562
PCT Pub. Date: May 7, 2015

(65) Prior Publication Data
US 2016/0251360 A1   Sep. 1, 2016

(30) Foreign Application Priority Data
Nov. 1, 2013   (CZ) ..................... 2013-842

(51) Int. Cl.
C07D 487/04   (2006.01)
A61K 31/4985   (2006.01)
C07C 59/255   (2006.01)

(52) U.S. Cl.
CPC .......... *C07D 487/04* (2013.01); *C07C 59/255* (2013.01); *C07B 2200/13* (2013.01)

(58) Field of Classification Search
None
See application file for complete search history.

(56) References Cited

U.S. PATENT DOCUMENTS 6,699,871 B2   3/2004   Edmondson et al.

FOREIGN PATENT DOCUMENTS

| EP | 1654263 | 5/2006 |
|---|---|---|
| EP | 1909776 | 4/2008 |
| WO | WO-03/004498 | 1/2003 |
| WO | WO-2005/072530 | 8/2005 |
| WO | WO-2009/085990 | 7/2009 |

OTHER PUBLICATIONS

Gu et al. J.Pharmaceutical Sciences, Nov. 2001 vol. 90, Issue 11, pp. 1878-1890 (Abstract).*
IP.com Journal, Anonymous author, vol. 14 (5B), pp. 1-12 (May 7, 2014).*

* cited by examiner

*Primary Examiner* — Emily Bernhardt
(74) *Attorney, Agent, or Firm* — Pearl Cohen Zedek Latzer Baratz LLP

(57) ABSTRACT

A stable polymorph (Form Z1) of the salt of (2R)-4-oxo-4-[3-(trifluoromethyl)-5,6-dihydro [1s2,4]triazolo[4,3-α]pyrazin-7(8H)-yl]-1-(2s4,5-trifluorophenyl)butan-2-amine (sitagliptin) with L-tartaric acid, of formula 1, which is a very suitable form of the active pharmaceutical ingredient of medicinal products intended especially for treatment of diabetes type 2. A method of preparation of the stable polymorph (Form Z1) of the salt of sitagliptin with L-tartaric acid, as well as its use for the preparation of a pharmaceutical composition.

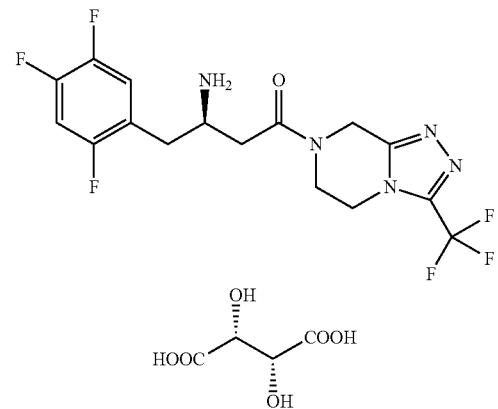

5 Claims, 4 Drawing Sheets

STABLE POLYMORPH OF THE SALT OF (2R)-4-OXO-4-[3-(TRIFLUOROMETHYL)-5,6-DIHYDRO[1,2,4]TRIAZOLO[4,3-α]PYRAZIN-7(8H)-YL]-1-(2,4,5-TRIFLUOROPHENYL)BUTAN-2-ANIME WITH L-TARTARIC ACID

CROSS-REFERENCE TO RELATED APPLICATIONS

This application is a National Phase Application of PCT International Application No. PCT/CZ2014/000125, International Filing Date Oct. 30, 2014, published as WO 2015/062562 on May 7, 2015, claiming priority of Czech Republic Patent Application No. PV 2013-842, filed Nov. 1, 2013, which are hereby incorporated by reference.

TECHNICAL FIELD (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine (sitagliptin) is used for treatment and prevention of diseases and conditions that are influenced by the dipeptidyl peptidase-4 (DPP-4) inhibitors. A typical example is diabetes mellitus type 2, obesity or high blood pressure. In pharmacology, sitagliptin is used in the form of the salt with phosphoric acid.

BACKGROUND ART

Patent documents U.S. Pat. No. 6,699,871 (issued in 2004) and WO 2003/004498 describe derivatives of beta-amino tetrahydrotriazolo-[4,3-α]pyrazine that are strong dipeptidyl peptidase-4 (DPP-4) inhibitors. The two above mentioned patent documents also particularly mention (2R)-4-oxo-4-[3-(trifluoromethyl)-5,6-dihydro[1,2,4]triazolo[4,3-α]pyrazin-7(8H)-yl]-1-(2,4,5-trifluorophenyl) butan-2-amine (sitagliptin). The scope of the above mentioned patent documents generally comprises also salts. However, the above mentioned patent documents did not mention any particular salts.

Some pharmaceutically acceptable salts of sitagliptin and their preparation are described in the patent applications EP 1 654 263 (2004), EP 1 909 776 (2006) and WO2009/085990. The patent application WO 2005/072530 relates to other salts of sitagliptin, including the salt with tartaric acid and its crystalline form.

DISCLOSURE OF INVENTION

The invention provides a new, stable polymorph (Form Z1) of the salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine (sitagliptin) with L-tartaric acid, of formula 1, which is a very suitable form of the active pharmaceutical ingredient of medicinal products intended especially for treatment of diabetes type 2.

Formula 1

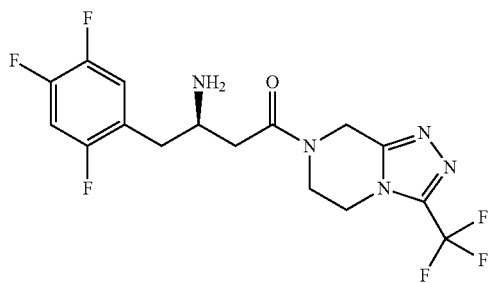

-continued

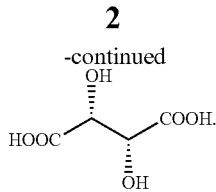

The invention further provides a method of preparation of a stable polymorph (Form Z1) of the salt of sitagliptin with L-tartaric acid, as well as its use for the preparation of a pharmaceutical composition.

DETAILED DESCRIPTION OF THE INVENTION

The present invention introduces a new, stable polymorph (Form Z1) of the salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine (sitagliptin) with L-tartaric acid, characterized by the following reflections in the X-ray powder pattern: 5.9; 9.8; 14.2; 19.5; 23.8 and 26.2±0.2° 2-theta, at the following parameters: radiation used CuKα (λ=1.542 Å=0.1542 nm, excitation voltage: 45 kV, anode current: 40 mA, measured range: 2-40° 2θ, increment: 0.01° 2θ. The above mentioned crystalline form of the salt of sitagliptin with L-tartaric acid exhibits the melting point of 201 to 204° C.

Polymorphism, occurrence of different crystalline forms, is a property of some molecules and molecular complexes (solvates, cocrystals, coordination compounds). Compounds such as salts of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine (sitagliptin) may create more crystalline forms having different physical characteristics manifested, e.g., by a different melting point, X-ray diffraction pattern, record of the thermogravimetric analysis ("TGA") or differential scanning calorimetry ("DSC"). Individual polymorphs also exhibit different stabilities. Less stable forms may then pass into more stable crystalline forms under suitable conditions. One of the most important characteristics of active pharmaceutical compounds is their solubility in water, which influences their biological availability to a considerable extent. Different crystalline forms of the same pharmaceutical compound may have and in most cases also have different solubilities and thus also different biological availabilities. For these reasons it is absolutely necessary to guarantee, besides the chemical stability of the pharmaceutical compound, also the stability of the particular crystalline form.

When studying the properties of salts of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine (sitagliptin), a quite new polymorph (Form Z1) of the salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine (sitagliptin) with L-tartaric acid has been successfully obtained, characterized by the following reflections in the X-ray powder pattern: 5.9; 9.8; 14.2; 19.5; 23.8 and 26.2±0.2° 2-theta. It has been surprisingly found out in further experiments that the previously described crystalline form of this salt (published in WO 2005/072530), characterized by the following reflections in the X-ray powder pattern: 5.8; 12.9; 16.1; 18.0; 21.3; 23.4 and 26.2±0.2° 2-theta, was significantly less stable than the new crystalline form (Form Z1) of the salt of (2R)-4-oxo-4-[3-(trifluoromethyl)-5,6-dihydro[1,2,4]triazolo[4,3-α]pyrazin- 7(8H)-yl]-1-(2,4,5-trifluorophenyl)butan-2-amine (sitagliptin) with L-tartaric acid, discovered by us, characterized by the following reflections in the X-ray powder pattern: 5.9; 9.8; 14.2; 19.5; 23.8 and 26.2±0.2° 2-theta. It has been quite unexpectedly found out that already in case of an inconsiderable contamination of the original polymorph by our new, more stable crystalline form (Form Z1) a very quick transformation of the original polymorph to our new, more stable polymorph (Form Z1) occurs, characterized by the following reflections in the X-ray powder pattern: 5.9; 9.8; 14.2; 19.5; 23.8 and 26.2±0.2° 2-theta, even under the conditions in which the original crystalline form characterized by the following reflections in the X-ray powder pattern: 5.8; 12.9; 16.1; 18.0; 21.3; 23.4 and 26.2±0.2° 2-theta is prepared.

The new stable polymorph of sitagliptin L-tartrate (Form Z1) can be conveniently prepared by dissolution of the sitagliptin free base in a suitable organic solvent or a mixture of two or more organic solvents and addition of a solution of L-tartaric acid dissolved in a suitable organic solvent or water. What is especially advantageous is dissolution of sitagliptin free base in a polar solvent, especially in a solvent from the group of C1-C5 alkyl alcohols or their mixture, or their mixture with water, and dissolution of L-tartaric acid in a polar solvent, especially in a solvent from the group of C1-C5 alkyl alcohols or in water or in a mixture of C1 -C5 alkyl alcohols or a mixture of one of the C1 -C5 alkyl alcohols with water. An especially advantageous embodiment comprises the addition of a small amount of the pre-prepared polymorph Z1 into a solution of the sitagliptin free base or to a solution of L-tartaric acid, just before mixing of the solution of sitagliptin with the solution of the L-tartaric acid. A favorable step for the preparation of the stable polymorph of sitagliptin L-tartrate (Form Z1) is heating up of this mixture to an elevated temperature, especially to a temperature in the range of from 25° C. to the boiling point of the solvent used or a mixture of solvents at the given pressure, particularly to a temperature between 50 and 82° C., or repeated heating up to this temperature.

The new stable polymorph of sitagliptin L-tartrate (Form Z1) can also be conveniently prepared by suspending of sitagliptin L-tartrate, prepared in accordance with the patent document WO 2005/072530, in a suitable organic solvent or a mixture of 2 or more organic solvents or a mixture of an organic solvent with water and mixing of this suspension for a necessary time period. An especially advantageous embodiment consists in suspending sitagliptin L-tartrate obtained in accordance with WO 2005/072530 in a polar solvent, especially in a solvent from the group of C1-C5 alkyl alcohols or their mixture, or their mixture with water and with addition of a small amount of the pre-prepared polymorph Z1. What is favorable for the preparation of the stable polymorph of sitagliptin L-tartrate (Form Z1) is heating up of the suspension of L-tartrate obtained by the process of WO 2005/072530 with a small addition of sitagliptin L-tartrate (Form Z1) to an elevated temperature, especially to a temperature in the range of from 25° C. to the boiling point of the solvent used or a mixture of solvents at the given pressure, particularly to a temperature between 50 and 82° C., or repeated heating up to this temperature.

LIST OF ANALYTIC METHODS

X-Ray

Figure 1:
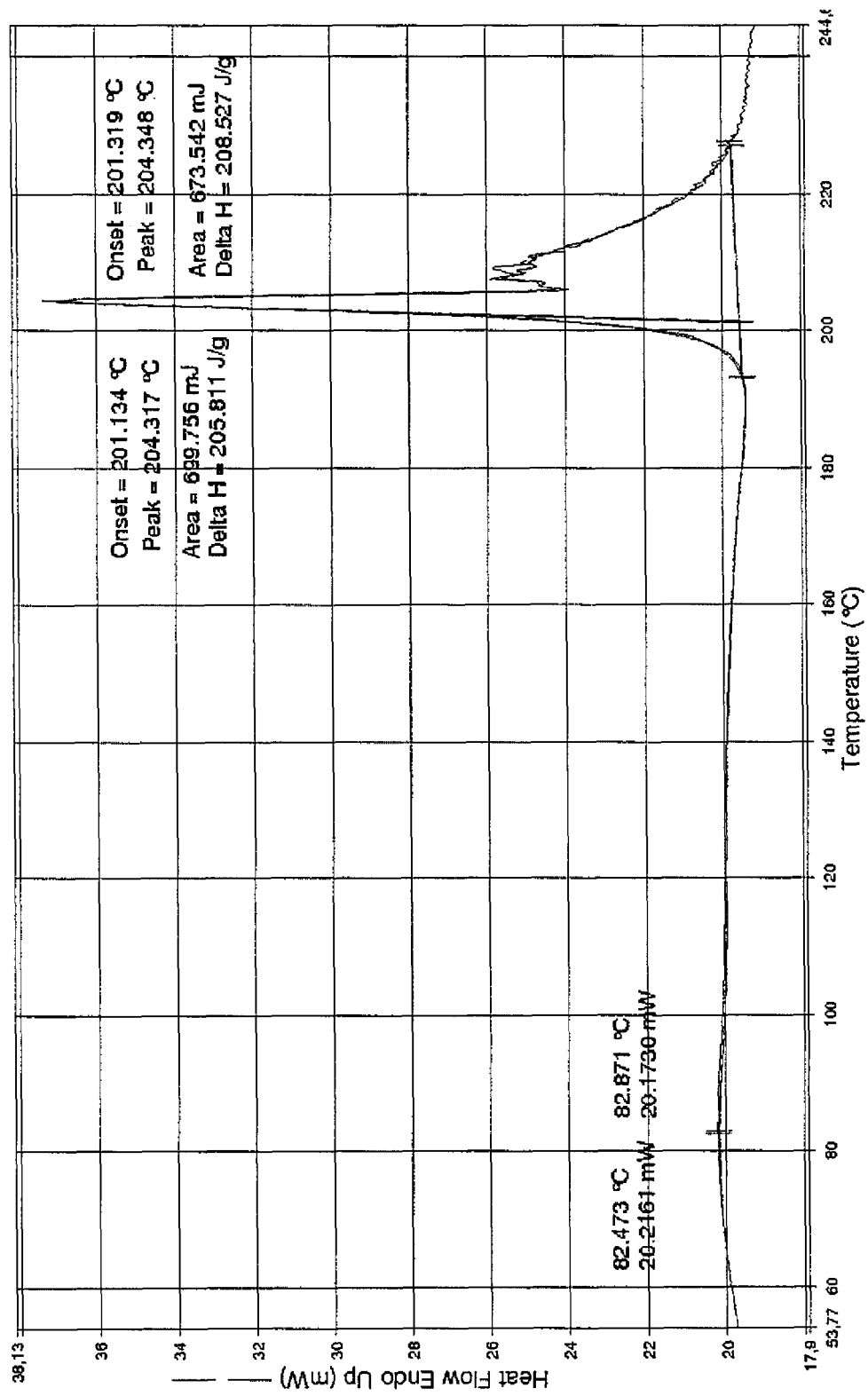
FIG. 1: DSC record of Form Z1 of sitagliptin L-tartrate
Figure 2:
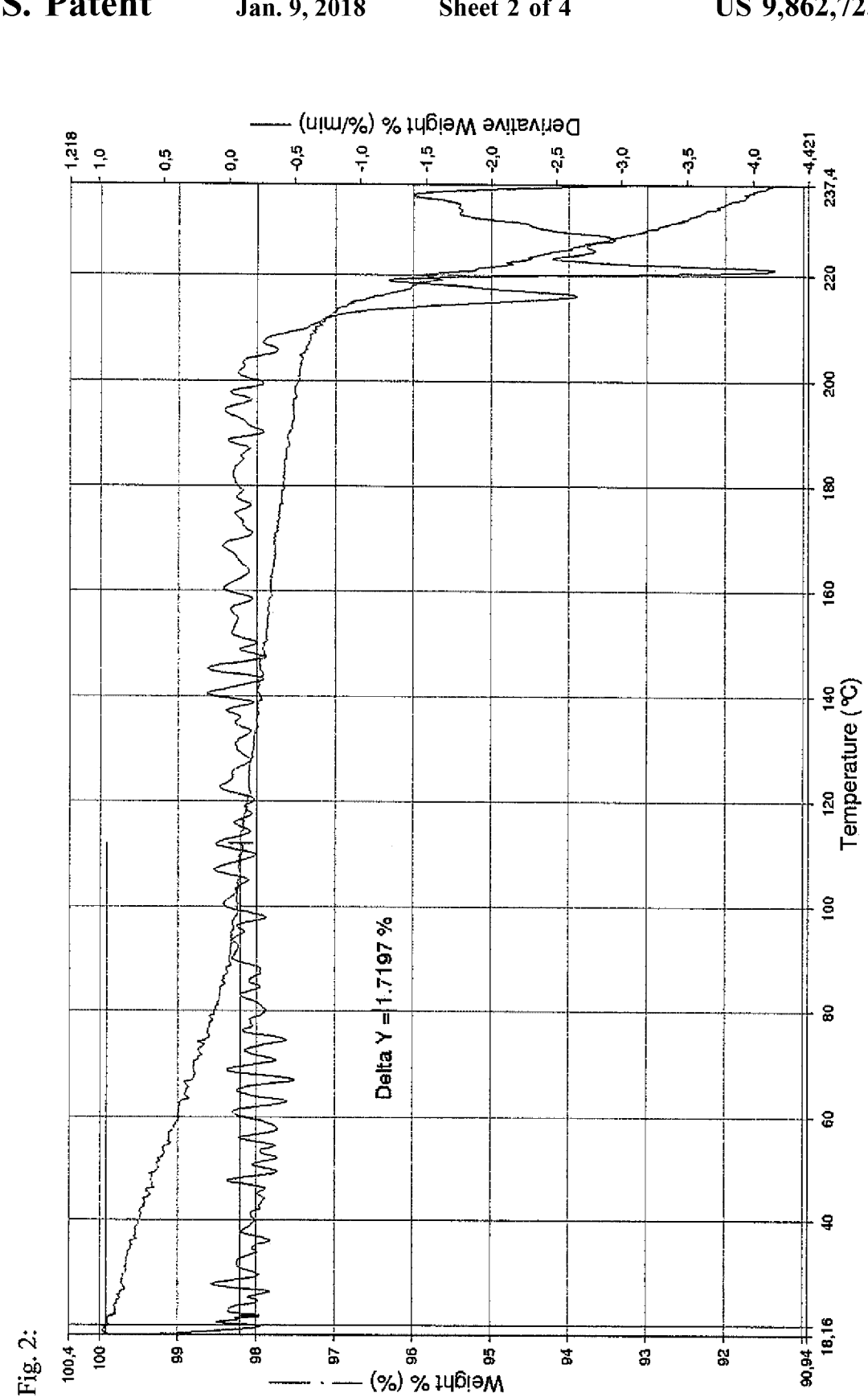
FIG. 2: TGA record of Form Z1 of sitagliptin L-tartrate
Figure 3:
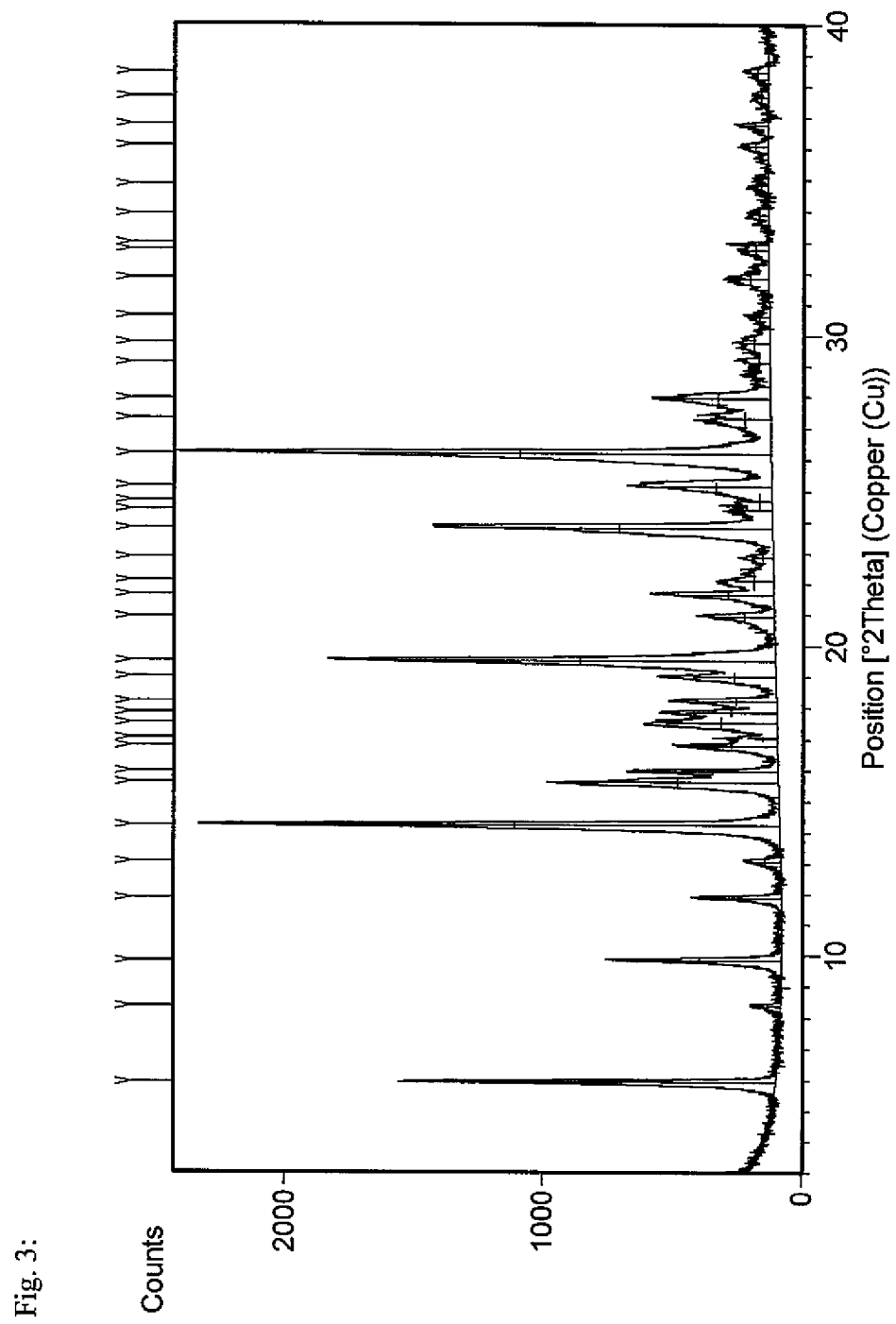
FIG. 3: X-ray diffraction pattern of the polymorph Z1 of sitagliptin L-tartrate
Figure 4:
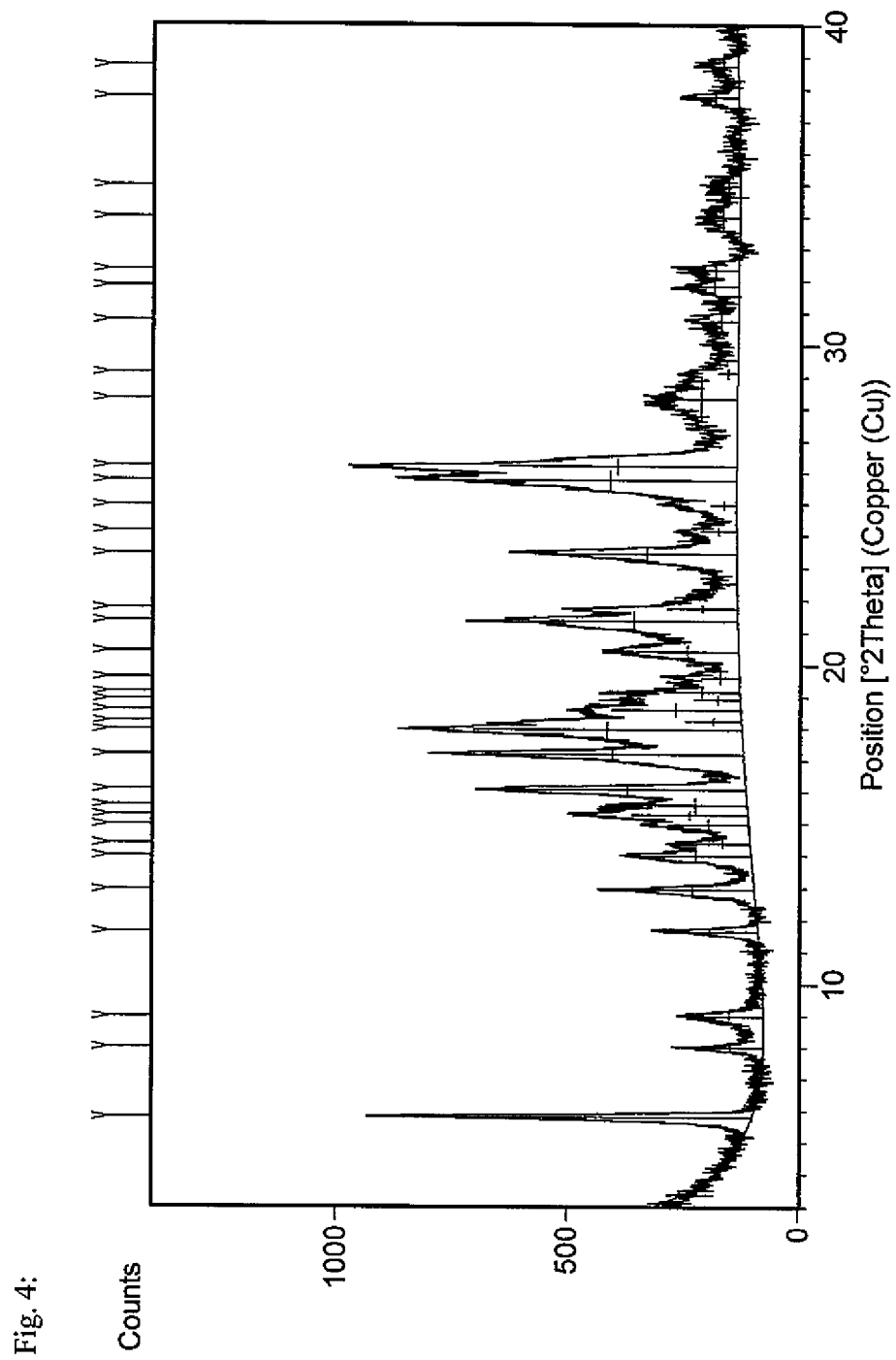
FIG. 4: X-ray diffraction pattern of sitagliptin L-tartrate described in WO 2005/072530

Measurement parameters of XRPD: The diffraction pattern was measured using an X'PERT PRO MPD PANalytical diffractometer, radiation used CuKα ($\lambda$=1.542 Å=0.1542 nm), excitation voltage: 45 kV, anode current: 40 mA, measured range: 2-40° 2θ, increment: 0.01° 2θ. For the measurement a flat powder sample was used that was placed on a Si plate. For the setting of the primary optical equipment programmable divergence slits with the irradiated area of the sample of 10 mm, 0.02 rad Soller slits and a ¼° anti-diffusion slit were used. For the setting of the secondary optical equipment an X'Celerator detector with maximum opening of the detection slot, 0.02 rad Soller slits and a 5.0 mm anti-diffusion slit were used.

DSC

The records of the differential scanning calorimetry were measured using a DSC Pyris 1 device from Perking Elmer. The sample charge in a standard Al pot (20 µL) was between 3 and 4 mg and the heating rate was 10° C./min. The temperature program that was used consists of 1 min stabilization at the temperature of 50° C. and then of heating up to 250° C. at the heating rate of 10° C./min. 4.0 $N_2$ was used as the carrier gas at the flow rate of 20 ml/min.

TGA:

The thermogravimetric (TGA) record was measured using a Perkin Elmer TGA 6 device. The samples were weighed into ceramic pots and measured in a nitrogen stream ($4N_2$ 20 ml/min). The TGA measurements were conducted in the temperature range of from 20° C. to 250° C. at the heating up rate of 10° C./min. The weight of the samples varied around 20.9 mg.

EXAMPLES

Example 1

Reference Example

Preparation of the Salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine with L-tartaric acid in accordance with WO2005/072530 (page 15, Example 2)

Sitagliptin free base (9 g) was dissolved in 450 ml of propan-2-ol by heating up to 50° C. L-tartaric acid dissolved in demineralized water (3.37 g in 45 ml) was added to the clear solution. The thick white suspension that was separated in a few minutes was stirred at 60° C. for 18 hours. After cooling and filtration the obtained salt of sitagliptin with tartaric acid was washed with propan-2-ol and dried in a vacuum drier at 40° C. 12 g of a colorless product with the water content of 1.6% was obtained. The obtained polymorph was characterized by means of XRPD.

Table of diffraction peaks:

| Pos. [°2Th.] | d-spacing [nm] | Rel. Int. [%] |
|---|---|---|
| 5.82 | 1.5166 | 100.0 |
| 8.01 | 1.1036 | 18.1 |
| 8.96 | 0.9866 | 20.6 |
| 11.66 | 0.7585 | 32.4 |

-continued

| Pos. [°2Th.] | d-spacing [nm] | Rel. Int. [%] |
|---|---|---|
| 12.93 | 0.6840 | 40.2 |
| 13.99 | 0.6324 | 36.6 |
| 15.26 | 0.5801 | 33.8 |
| 16.05 | 0.5519 | 78.9 |
| 17.17 | 0.5161 | 87.2 |
| 17.99 | 0.4926 | 92.0 |
| 18.62 | 0.4761 | 42.8 |
| 20.45 | 0.4340 | 34.4 |
| 21.35 | 0.4159 | 68.5 |
| 21.74 | 0.4085 | 23.6 |
| 23.43 | 0.3794 | 59.0 |
| 25.80 | 0.3451 | 92.4 |
| 26.17 | 0.3402 | 94.5 |
| 28.26 | 0.3156 | 21.9 |
| 31.81 | 0.2811 | 14.4 |
| 32.33 | 0.2767 | 13.9 |
| 37.75 | 0.2381 | 15.3 |

Example 2

Preparation of the New Polymorph (Form Z1) of the Salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine with L-tartaric acid Sitagliptin free base (9 g) was dissolved in a mixture of 400 ml of propan-2-ol and 50 ml of methanol by heating up to 50° C. L-tartaric acid dissolved in demineralized water (3.37 g in 45 ml) was added to the clear solution. The thick white suspension that was separated in a few minutes was agitated at 50° C. for 1 h and then cooled at the rate of 5° C./h down to the room temperature (20° C.). After cooling and filtration the obtained salt of sitagliptin with tartaric acid was washed with a small amount of propan-2-ol and dried in a vacuum drier at 40° C. 11.8 g of a colorless product with the water content of 1.7% was obtained. The obtained polymorph Z1 was characterized by means of XRPD, DSC and TGA.

Table of diffraction peaks:

| Pos. [°2Th.] | d-spacing [nm] | Rel. Int. [%] |
|---|---|---|
| 5.93 | 1.4880 | 63.5 |
| 8.37 | 1.0557 | 5.1 |
| 9.82 | 0.8999 | 30.9 |
| 11.88 | 0.7443 | 15.6 |
| 13.08 | 0.6766 | 6.0 |
| 14.23 | 0.6219 | 100.0 |
| 15.61 | 0.5673 | 37.9 |
| 15.97 | 0.5545 | 24.6 |
| 16.79 | 0.5277 | 17.5 |
| 17.51 | 0.5060 | 21.0 |
| 17.86 | 0.4963 | 17.2 |
| 18.22 | 0.4865 | 15.4 |
| 19.00 | 0.4667 | 15.6 |
| 19.52 | 0.4545 | 73.6 |
| 20.93 | 0.4241 | 11.2 |
| 21.65 | 0.4102 | 17.2 |
| 23.82 | 0.3733 | 57.7 |
| 25.16 | 0.3537 | 20.8 |
| 26.17 | 0.3403 | 94.5 |
| 27.29 | 0.3265 | 9.7 |
| 27.93 | 0.3192 | 19.4 |
| 31.85 | 0.2808 | 7.0 |

Example 3

Preparation of the Salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine with L-tartaric acid (Form Z1) Sitagliptin free base (9 g) was dissolved in 450 ml of propan-2-ol by heating up to 50° C. 50 mg of the polymorph Z1 prepared in accordance with Example 2 was added to the clear solution and then L-tartaric acid dissolved in demineralized water (3.37 g in 45 ml) was added. The thick white suspension that was separated very quickly was agitated at 60° C. for 1 h and then cooled at the rate of 5° C./min down to the room temperature (20° C.). After cooling and filtration the obtained salt of sitagliptin with L-tartaric acid was washed with a small amount of propan-2-ol and dried in a vacuum drier at 40° C. 12 g of a colorless product with the water content of 1.7% was obtained. The obtained polymorph was characterized by means of XRPD, DSC and TGA.

Example 4

Preparation of the Salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine with L-tartaric acid (Mixture of Forms) The salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine (sitagliptin) with L-tartaric acid, prepared in accordance with Example 1 (according to WO 2005/072530) (2 g) was suspended in propan-2-ol (50 ml) and the suspension was heated up to 50° C. under constant agitation. The polymorph Z1 (0.1 g) prepared in accordance with Example 2 was added to the white suspension. The mixture was agitated at the same temperature for 20 minutes and after cooling to 20° C. the product was filtered off and washed with a small amount of propan-2-ol. The obtained product was dried in a vacuum drier at 40° C. 1.9 g of a mixture of forms was obtained, Form Z1 being enriched considerably.

Example 5

Preparation of the Salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine with L-tartaric acid (Form Z1) The mixture of the polymorphic forms of sitagliptin L-tartrate prepared in accordance with Example 4 (1.1 g) was suspended in 2 ml of demineralized water. The suspension was agitated at the room temperature (20° C.) for 5 minutes and then diluted with 20 ml of propan-2-ol. The thick suspension was heated up to 60° C. At this temperature it was agitated for 10 minutes and then cooled at the rate of 20° C./h down to the room temperature (20° C.). The product was filtered off and washed with a small amount of propan-2-ol. The obtained product was dried in a vacuum drier at 40° C. 1.0 of the pure Form Z1 with the water content of 1.6% was obtained. The obtained polymorph was characterized by means of XRPD, DSC and TGA.

What is claimed is:

1. A solid crystalline form of the salt of sitagliptin with L-tartaric acid, wherein the x-ray powder pattern of the solid crystalline form of the salt of sitagliptin with L-tartaric acid consists of the following peaks:

| Pos. [°2 Th.] | d-spacing [nm] | Rel. Int. [%] |
|---|---|---|
| 5.93 | 1.4880 | 63.5 |
| 8.37 | 1.0557 | 5.1 |
| 9.82 | 0.8999 | 30.9 |

-continued

| Pos.<br>[°2 Th.] | d-spacing<br>[nm] | Rel. Int.<br>[%] |
|---|---|---|
| 11.88 | 0.7443 | 15.6 |
| 13.08 | 0.6766 | 6.0 |
| 14.23 | 0.6219 | 100.0 |
| 15.61 | 0.5673 | 37.9 |
| 15.97 | 0.5545 | 24.6 |
| 16.79 | 0.5277 | 17.5 |
| 17.51 | 0.5060 | 21.0 |
| 17.86 | 0.4963 | 17.2 |
| 18.22 | 0.4865 | 15.4 |
| 19.00 | 0.4667 | 15.6 |
| 19.52 | 0.4545 | 73.6 |
| 20.93 | 0.4241 | 11.2 |
| 21.65 | 0.4102 | 17.2 |
| 23.82 | 0.3733 | 57.7 |
| 25.16 | 0.3537 | 20.8 |
| 26.17 | 0.3403 | 94.5 |
| 27.29 | 0.3265 | 9.7 |
| 27.93 | 0.3192 | 19.4 |
| 31.85 | 0.2808 | 7.0. |

2. The crystalline form of the salt of sitagliptin with L-tartaric acid according to claim 1, wherein its melting point is 201 to 204° C.

3. A process of preparing the crystalline form of Sitagliptin L-tartrate as defined in claim 1, comprising dissolving sitagliptin free base in a mixture of propan-2-ol and methanol, dissolving L-tartaric acid in water, heating the prepared mixture to a temperature of from 40 to 60° C., and subsequently cooling the prepared mixture at the rate of 5° C./hour down to the room temperature.

4. A pharmaceutical composition comprising the crystalline form of the salt of sitagliptin with L-tartaric acid as defined in claim 1.

5. A process of preparing the crystalline form of Sitagliptin L-tartrate as defined in claim 1, wherein a suspension of sitagliptin L-tartrate, having the following diffraction peaks in XRPD:

| Pos.<br>[°2 Th.] | d-spacing<br>[nm] | Rel. Int.<br>[%] |
|---|---|---|
| 5.82 | 1.5166 | 100.0 |
| 8.01 | 1.1036 | 18.1 |
| 8.96 | 0.9866 | 20.6 |
| 11.66 | 0.7585 | 32.4 |
| 12.93 | 0.6840 | 40.2 |
| 13.99 | 0.6324 | 36.6 |
| 15.26 | 0.5801 | 33.8 |
| 16.05 | 0.5519 | 78.9 |
| 17.17 | 0.5161 | 87.2 |
| 17.99 | 0.4926 | 92.0 |
| 18.62 | 0.4761 | 42.8 |
| 20.45 | 0.4340 | 34.4 |
| 21.35 | 0.4159 | 68.5 |
| 21.74 | 0.4085 | 23.6 |
| 23.43 | 0.3794 | 59.0 |
| 25.80 | 0.3451 | 92.4 |
| 26.17 | 0.3402 | 94.5 |
| 28.26 | 0.3156 | 21.9 |
| 31.81 | 0.2811 | 14.4 |
| 32.33 | 0.2767 | 13.9 |
| 37.75 | 0.2381 | 15.3 | in a solvent or a mixture of solvents is heated with a small addition of sitagliptin L-tartrate as defined in claim 1 to a temperature in the range of from 25° C. to the boiling point of the solvent or the mixture of solvents, wherein the solvent or mixture of solvents is composed of at least one $C_1$-$C_5$ alkyl alcohol, water, or any combination thereof.

* * * * *